US010591480B2

(12) United States Patent
Heinz et al.

(10) Patent No.: US 10,591,480 B2
(45) Date of Patent: Mar. 17, 2020

(54) METHOD FOR THE DETECTION OF AN IGM ANTIBODY SPECIFIC FOR A FLAVIVIRUS IN A SAMPLE

(71) Applicant: MEDIZINISCHE UNIVERSITÄT WIEN, Vienna (AT)

(72) Inventors: Franz X. Heinz, Vienna (AT); Karin Stiasny, Vienna (AT)

(73) Assignee: MEDIZINISCHE UNIVERSITÄT WIEN, Vienna (AT)

( * ) Notice: Subject to any disclaimer, the term of this patent is extended or adjusted under 35 U.S.C. 154(b) by 0 days.

(21) Appl. No.: 16/307,710

(22) PCT Filed: Jun. 2, 2017

(86) PCT No.: PCT/EP2017/063446
§ 371 (c)(1),
(2) Date: Dec. 6, 2018

(87) PCT Pub. No.: WO2017/211713
PCT Pub. Date: Dec. 14, 2017

(65) Prior Publication Data
US 2019/0170750 A1    Jun. 6, 2019

(51) Int. Cl.
G01N 33/569 (2006.01)
G01N 33/00 (2006.01)

(52) U.S. Cl.
CPC . G01N 33/56983 (2013.01); G01N 2333/185 (2013.01); G01N 2469/20 (2013.01); Y02A 50/53 (2018.01)

(58) Field of Classification Search
CPC .............. A61K 2300/00; A61K 45/06; A61K 2039/505; A61K 39/12; A61K 38/162; A61K 39/00; C07K 16/1063; C07K 16/1081; G01N 33/56983; G01N 33/6854; G01N 33/6857; A61L 2420/06; A61L 29/08; G06T 7/41
See application file for complete search history.

(56) References Cited

U.S. PATENT DOCUMENTS

| | | | |
|---|---|---|---|
| 4,366,241 | A | 12/1982 | Tom et al. |
| 4,843,000 | A | 6/1989 | Litman et al. |
| 4,849,338 | A | 7/1989 | Litman et al. |
| 5,077,391 | A | 12/1991 | Raison et al. |
| 5,112,952 | A | 5/1992 | Mallia et al. |

FOREIGN PATENT DOCUMENTS

| | | |
|---|---|---|
| EP | 0752425 | 1/1997 |
| EP | 2980099 | 2/2016 |
| WO | WO 98/26794 | 12/1997 |
| WO | WO 99/06068 | 2/1999 |
| WO | WO 2001/002001 | 1/2001 |
| WO | WO 2004/052293 | 6/2004 |
| WO | WO 2006/115548 | 11/2006 |
| WO | WO 2008/152528 | 12/2008 |
| WO | WO 2011/004324 | 1/2011 |
| WO | WO 2016/012800 | 1/2016 |
| WO | WO 2016/022071 | 2/2016 |
| WO | WO 2016/059018 | 4/2016 |

OTHER PUBLICATIONS

Angel Balmaseda et al. Clin Diagn Lab Immunol. Mar. 2003; 10(2) 317-322.*
Andrea J. Cuzzubbo et al. J Clin Microbiol. Nov. 1999; 37(11) 3738-3741.*
Allison et al., "Oligomeric rearrangement of tick-borne encephalitis virus envelope proteins induced by an acidic pH," J. Virol., 1995, 69:695-700.
Dai et al., "Structures of the Zika Virus Envelope Protein and Its Complex with a Flavivirus Broadly Protective Antibody," Cell Host & Microbe, 2016, 19:696-704.
Elshuber et al., "Cleavage of protein prM is necessary for infection of BHK-21 cells by tick-borne encephalitis virus" J. Gen Virol., 2003, 84:183-191.
Heinz et al., "Comparison of Two Different Enzyme Immunoassays for detection of Immunoglobulin M Antibodies Against Tick-Borne Encephalitis Virus in Serum and cerebrospinal Fluid," Journal of Clinical Microbiology, 1981, 14(2):141-146.
Heinz et al., "Homogeneity of the Structural Glycoprotein from European Isolates of Tick-borne Encephalitis Virus: Comparison with Other Flaviviruses," J. Gen. Virol., 1981, 57:263-274.
Heinz et al., "The Flavivirus Envelope Protein E: Isolation of a Soluble Form from Tick-Borne Encephalitis Virus and Its Crystallization," Journal of Virology, 1991, 65(10):5579-5583.
International Search Report and Written Opinion issued in International Patent Application No. PCT/EP2017/063446, dated Jul. 7, 2018.
Jarmer et al., "Variation of the Specificity of the Human Antibody Responses after Tick-Borne Encephalitis Virus Infection and Vaccination," Journal of virology, 2014, 88(23):13845-13857.
Kanai et al., "Crystal Structure of West Nile Virus Envelope Glycoprotein Reveals Viral surface Epitopes," J. Virol., 2006, 80:11000-11008.
Kimple et al., "Overview of Affinity Tags for Protein Purification," Curr Protoc Protein Sci, 2015, 73, 26 Pages.
Koppel & Solomon, "IgM detection via selective recognition by mannose-binding protein," J. Biochem. Biophs. Methods, 2001, 49:641-647.

(Continued)

Primary Examiner — Bao Q Li
(74) Attorney, Agent, or Firm — Norton Rose Fulbright US LLP

(57) ABSTRACT

Disclosed is a method for the detection of an IgM antibody specific for a flavivirus in a sample, comprising the steps of (a) contacting the sample with a solid support comprising immobilised IgM-binding molecules, (b) allowing binding of IgM antibodies in the sample to the IgM binding molecules on the solid support so that the IgM antibodies are also immobilised on the solid support, and (c) detecting IgM antibodies specific for a flavivirus by allowing binding of a complex comprising (i) an antiparallel dimer of soluble flavivirus Protein E (sE) and (ii) a marker and identifying the binding of the complex to the specific flavivirus IgM antibody by detecting the marker; and a kit suitable for performing the method.

20 Claims, 7 Drawing Sheets

(56) References Cited

OTHER PUBLICATIONS

Figure 1:
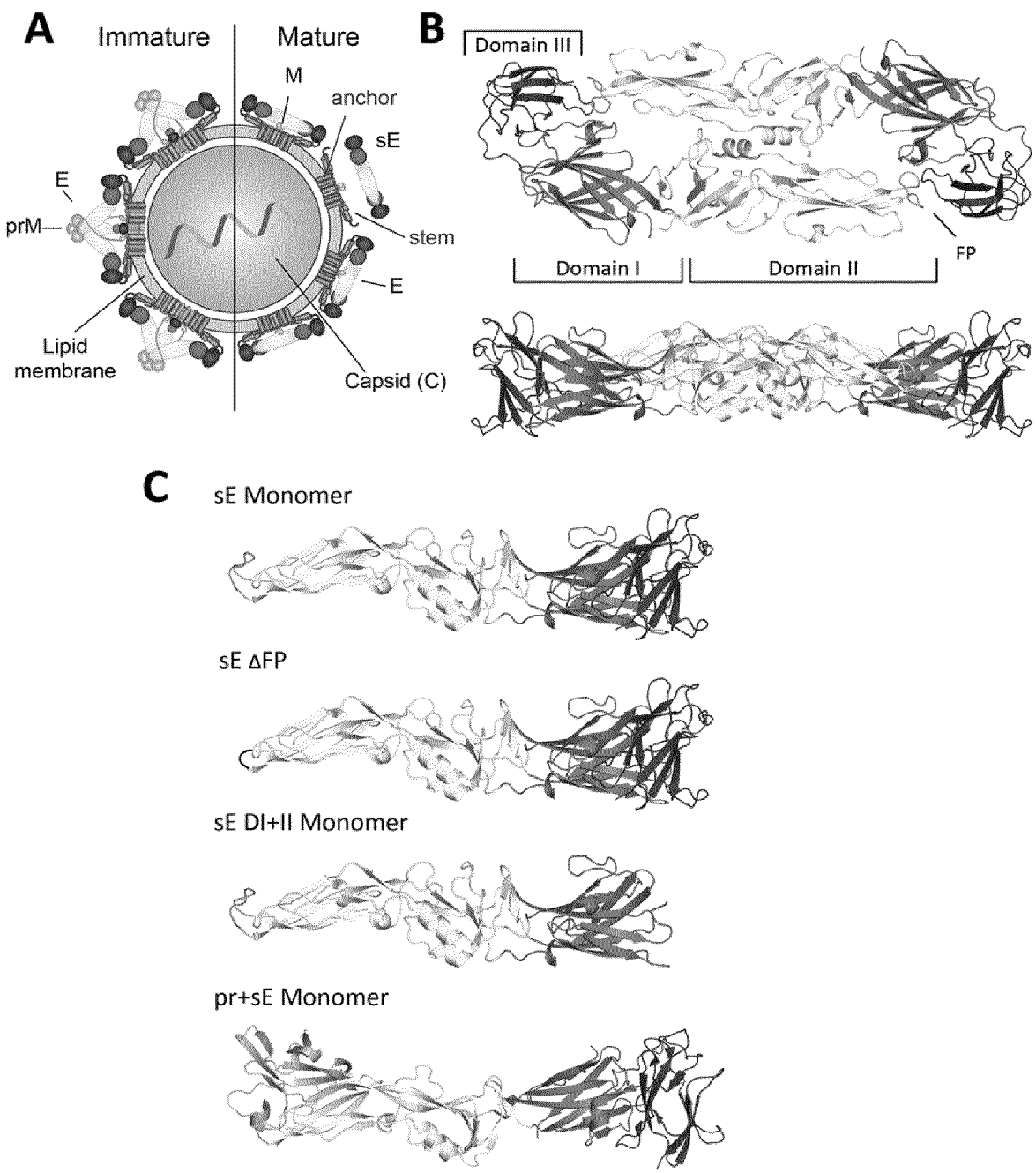

Li et al., "The flavivirus precursor membrane-envelope protein complex: structure and maturation," *Science*, 2008, 319:1830-1834.
Luca et al., "Crystal Structure of the Japanese Encephalitis Virus Envelope Protein," *Journal of Virology*, 2012, 86(4):2337-2346.
Maizel et al., "Polyacrylamide gel electrophoresis of viral proteins," *Methods Virol.*, 1971, 5:179-246.
Mandl et al., "Antigenic Structure of the Flavivirus Envelope Protein E at the Molecular Level, Using Tick-Borne Encephalitis Virus as a Model," *Journal of Virology*, 1989, 63(2):564-571.
Modis et al., "A ligand-binding pocket in the dengue virus envelope glycoprotein," *Proc Natl Acad Sci U.S.A.*, 2003, 100:6986-6991.
Modis et al., "Variable Surface Epitopes in the Crystal Structure of Dengue Virus Type 3 Envelope Glycoprotein," *Journal of Virology*, 2005, 79(2):1223-1231.
Musso et al., "Zika Virus," *Clinical Microbiology Reviews*, 2016, 29:487-524.
Nybakken et al., "Crystal Structure of the West Nile virus Envelope Glycoprotein," *J. Virol.*, 2006, 80:11467-11474.
Peeling et al., "Evaluation of diagnostic tests: dengue," *Nature Reviews Microbiology*, 2010, p. S30-S38.
Rey et al., "The envelope glycoprotein from tick-borne encephalitis virus at 2 A resolution." *Nature*, 1995, 375:291-298.
Rivetz et al., "New dengue antibody assay with unique differential detection of IgG and IgM antibodies" *Clin. Biochem.*, 2009, 42:180-184.
Shamala, DS, "Laboratory Diagnosis for Dengue: A Review" *The International Medical Journal of Malaysia*, 2015, 14(1):17-28.
Simmonds et al., "Family Flaviviridae" *Virus Taxonomy. IXth Report of International Committee on Taxonomy of Viruses*, 2011, p. 1003-1020.
Stiasny et al., "Quantitative determination of IgM antibodies reduces the pitfalls in the serodiagnosis of tick-borne encephalitis," *J Clin Virol.*, 2012, 54:115-120.
Tsouchnikas et al., "Immunization with Immune Complexes Modulates the Fine-Specificity of Antibody Responses to Flavivirus Antigen," *J Virol.*, 2015, 89(15):7970-7978.
Van Loon et al., "Direct Enzyme-Linked Immunosorbent Assay That Uses Peroxidase-Labeled Antigen for Determination of Immunoglobulin M Antibody to Cytomegalovirus," *Journal of Clinical Microbiology*, 1981, 13(3):416-422.
Van Loon et al., "Enzyme-Linked Immunosorbent Assay That Uses Labeled antigen for Detection of Immunoglobulin M and a Antibodies in Toxoplasmosis: Comparison with Indirect Immunofluorescence and Double-Sandwich Enzyme-Linked Immunosorbent Assay," *Journal of Clinical Microbiology*, 1983, 17(6): 997-1004.
Vogt et al., "Human monoclonal antibodies against West Nile virus induced by natural infection neutralize at a postattachment step," *Journal of Virology*, 2009, 83:6494-6507.
Vratskikh et al., "Dissection of Antibody Specificities Induced by Yellow Fever Vaccination," *PLOS Pathogens*, 2013, 9(6):e1003458.
Wood, David W., "New trends and affinity tag designs for recombinant protein purification," *Current Opinion in Plant Biology*, 2014, 26:54-61.
Zhang et al., "Conformational Changes of the Flavivirus E Glycoprotein," *Structure*, 2004, 12:1607-1618.
Zlatkovic et al., "Aluminum hydroxide influences not only the extent but also the fine specificity and functional activity of antibody responses to tick-borne encephalitis virus in mice," *J Virol*, 2013, 87:12187-12195.
Zlatkovic et al., "Immunodominance and functional activities of antibody responses to inactivated West Nile virus and recombinant subunit vaccines in mice," *J. Virol.*, 2011, 85:1994-2003.

\* cited by examiner

METHOD FOR THE DETECTION OF AN IgM ANTIBODY SPECIFIC FOR A FLAVIVIRUS IN A SAMPLE

CROSS-REFERENCE TO RELATED APPLICATIONS

This application is a national phase application under 35 U.S.C. § 371 of International Application No. PCT/EP2017/063446 filed 2 Jun. 2017, which claims priority to European Patent Application No. 16173043.7 filed 6 Jun. 2016. The entire contents of each of the above-referenced disclosures is specifically incorporated by reference herein without disclaimer.

The present invention relates to a method for the detection of an IgM antibody specific for a flavivirus in a sample.

Flavivirus infections are of global importance for human health, and provide—as the spread of Zika, dengue and West Nile virus illustrates—an increasing threat. Serological diagnosis of recent flavivirus infections requires immunoassays detecting specific IgM antibodies with high sensitivity. Various assay formats are in use for this purpose which are designed in different ways, for example: a) indirect ELISAs wherein the flavivirus antigen directly attached to a solid phase (for example, a microtiter plate) is incubated with the patient's serum and wherein the IgM antibodies bound to the immobilised antigen are detected by using an anti-human IgM antibody; b) M-Antibody-Capture (MAC) ELISA wherein the solid phase is coated with an anti-human IgM antibody and incubated with the patient's serum and wherein the detection of the specific IgM is performed by using the respective flavivirus antigen (WO2011/004324 A1, WO 2016/022071 A1).

An indirect ELISA for the detection of IgG antibodies after flaviviral immunizations is e.g. described in WO 99/06068 A2. The assay described therein uses the dimeric form of truncated dengue envelope protein as immobilised antigen for the detection of IgG antibodies against flaviviruses.

The advantage of the MAC ELISA compared to the indirect ELISA is the minimization of a possible interference with rheumatoid factors and other non-specific reactions as well as the interchangeability of antigens within the same test format.

This was highlighted in Van Loon et al. (J. Clin. Microbiol. 13 (1981): 416-422) and Van Loon et al. (J. Clin. Microbiol. 17 (1983): 997-1004) wherein the performance of direct MAC ELISAs for diagnosis of toxoplasma or cytomegalovirus infections, respectively, was compared to indirect ELISAs. Such a comparison was also disclosed in Heinz et al. (J. Clin. Microbiol. 14 (1981): 141-146), who confirmed that the MAC ELISA for detection of IgM antibodies against tick-borne encephalitis virus in serum and cerebrospinal fluid is more sensitive than an indirect ELISA.

Therefore, this test format has become the standard method for the serodiagnosis of dengue infections (Shamala 2015) and is recommended by WHO as a minimum requirement for diagnostic laboratories (Ref: WHO 2009). The most critical component for the quality of the MAC ELISA is the antigen and the method of its detection.

Test systems for detection of flavivirus infection in human patients are further disclosed in Revetz et al. (Clin. Biochem. 42 (2009), 180-184), WO 99/09414 A1, WO 2008/152528 A2 and EP 2980099 A1.

The major target of flavivirus neutralizing antibodies is the flavivirus envelope protein E, which is composed of three domains (DI, DII, DIII). It was found that the flavivirus neutralizing activity is mainly driven by antibodies directed to domains DI and DII of the E protein or to the E dimer structure (Jarmer et al., J. Virol. 88 (2014): 13845-13857). Another study assigned the flavivirus neutralizing activity upon yellow fever (YF) vaccination to antibodies directed to complex quaternary epitopes of the E protein displayed on the virion surface (Vratskikh et al., Plos Pathogens 9 (2013): e1003458).

Vogt et al. (J. Virol. 83(2009): 6494-6507) characterised two West Nile virus (WNV)-specific human monoclonal antibodies and disclosed that their neutralizing activity could be altered by mutations at the dimer interface in DII of the E protein, as well as at the hinge between DI and DII.

As a consequence, a number of immune compositions composed of different recombinant forms of the E protein have been developed for flavivirus vaccination (e.g. WO 2004/052293 A2, WO 2006/115548 A2, WO 2016/012800 A1).

While these studies are of importance for defining human IgG responses to the flavivirus E protein, they are not related to the serological diagnosis of flavivirus infections by the detection of IgM antibodies that are produced early in infection.

It is therefore an object of the present invention to provide an advantageous method for the detection of flavivirus-specific IgMs in patient samples, especially to provide improved MAC ELISAs for the detection of flavivirus-specific IgM antibodies for the detection of recent flavivirus infections.

Therefore, the present invention discloses a method for the detection of an IgM antibody specific for a flavivirus in a sample, comprising the steps of
(a) contacting the sample with a solid support comprising immobilised IgM-binding molecules,
(b) allowing binding IgM antibodies in the sample to the IgM binding molecules on the solid support so that the IgM antibodies are also immobilised on the solid support, and
(c) detecting IgM antibodies specific for a flavivirus by allowing binding of a complex comprising
  (i) an antiparallel dimer of soluble flavivirus Protein E (sE) and
  (ii) a marker
and identifying the binding of the complex to the specific flavivirus IgM antibody by detecting the marker.

The present invention further discloses a method for the detection of an IgM antibody specific for a flavivirus in a sample, comprising the steps of
(a) contacting the sample with a solid support comprising immobilised IgM-binding molecules,
(b) allowing binding of IgM antibodies in the sample to the IgM binding molecules on the solid support so that the IgM antibodies are also immobilised on the solid support, and
(c) premixing an antiparallel dimer of soluble flavivirus Protein E (sE) with a marker for formation of a complex comprising the sE dimer and the marker, and
(d) detecting IgM antibodies specific for a flavivirus by allowing binding of the preformed complex
and identifying the binding of the complex to the specific flavivirus IgM antibody by detecting the marker.

The present invention therefore provides a new detection system specifically suited for the MAC ELISA test format. Antigens used so far in flavivirus MAC ELISAs include virus preparations or recombinantly produced virus-like particles that are detected in a further step by a virus-specific antibody via an enzymatic reaction. On the one hand, the production of virus preparations requires the handling of highly infectious agents—in many cases of biosafety level 3—and their inactivation for commercial applications; virus-like particles on the other hand, are relatively expensive, difficult to purify, to produce and to standardize.

The MAC ELISA format is the specifically preferred format of the method and test system according to the present invention. The IgM test is of general importance for the diagnosis of flavivirus infections because the direct detection of virus (e.g. via PCR) is only possible in a narrow time window after an infection, and in many cases is already negative despite the presence of clinical symptoms. In the context of travel medicine, the virus will rarely be detectable upon return from a journey to flavivirus endemic regions. Accordingly, serology, in particular IgM detection, is very important for flavivirus diagnostics.

Among the most important human pathogenic flaviviruses are dengue viruses (serotypes 1 to 4) and the rapidly spreading Zika virus that circulate simultaneously in tropical and sub-tropical regions. Since these regions are also popular tourist destinations, reliable tests to differentiate these infections are not only of great importance in the endemic areas, but also in the traveller's home countries.

In comparison to existing MAC ELISA formats for detecting flavivirus IgMs, the diagnostic test system according to the present invention has several advantages: The assay according to the invention has excellent suitability for highly specific detection of flavivirus IgM antibodies, in particular dengue virus, Zika virus, tick borne encephalitis (TBE) virus. The data obtained in the course of the present invention also show that this test can not only perfectly distinguish between infections with Zika and dengue viruses, but is also suitable for the serotype-specific diagnosis of dengue virus infections (serotype 1 to 4). In addition, the method according to the present invention also enabled the detection of double infections, e.g. with dengue and Zika virus.

Moreover, due to the stability of the present test system and the reliable provision of its components (especially the complex comprising the sE dimer and the marker), the test system according to the present invention can effectively and reliably be standardized. In particular, the virus-specific antigen (soluble E protein) can be produced recombinantly in large quantities and highly purified form. For the production of sE, any recombinant system is suitable that allows native folding of sE (e.g. in HEK cells, CHO cells, 293 cells, Drosophila cells or baculovirus-based expression systems). Also the other components may be purchased commercially.

In contrast thereto, comparable test systems currently on the market use inactivated virus, infected cell lysates or recombinantly produced virus-like particles. The main disadvantage of inactivated viruses or cell lysates is that they require handling of viruses which are highly pathogenic for humans. The main disadvantages of virus-like particles (VLP, RSP, recombinant prM-E antigen) are (1) that there is no relatively simple approach for antigen purification (although recombinant production is possible); however, these antigens are used as a non-purified cell culture supernatant, which has the disadvantage that an additional reagent and an additional test step (namely, a virus-specific antibody and a corresponding antibody-detection reagent) are required and that for each virus test (dengue, Zika, TBE etc.), a specific antibody is necessary; (2) virus-like particles contain a lipid membrane and therefore are inherently prone to instability and therefore storage problems (in contrast to the extremely stable soluble antigens in the test according to the invention); (3) particles, in which the E proteins are anchored in the lipid membrane, are pH sensitive; in fact, at acidic pH values, the E proteins on the particle surface refold to a completely different shape, which leads to aggregation of the particles; accordingly, particulate forms of antigens, such as VLP, are very sensitive diagnostic antigens.

Figures 3, 4:
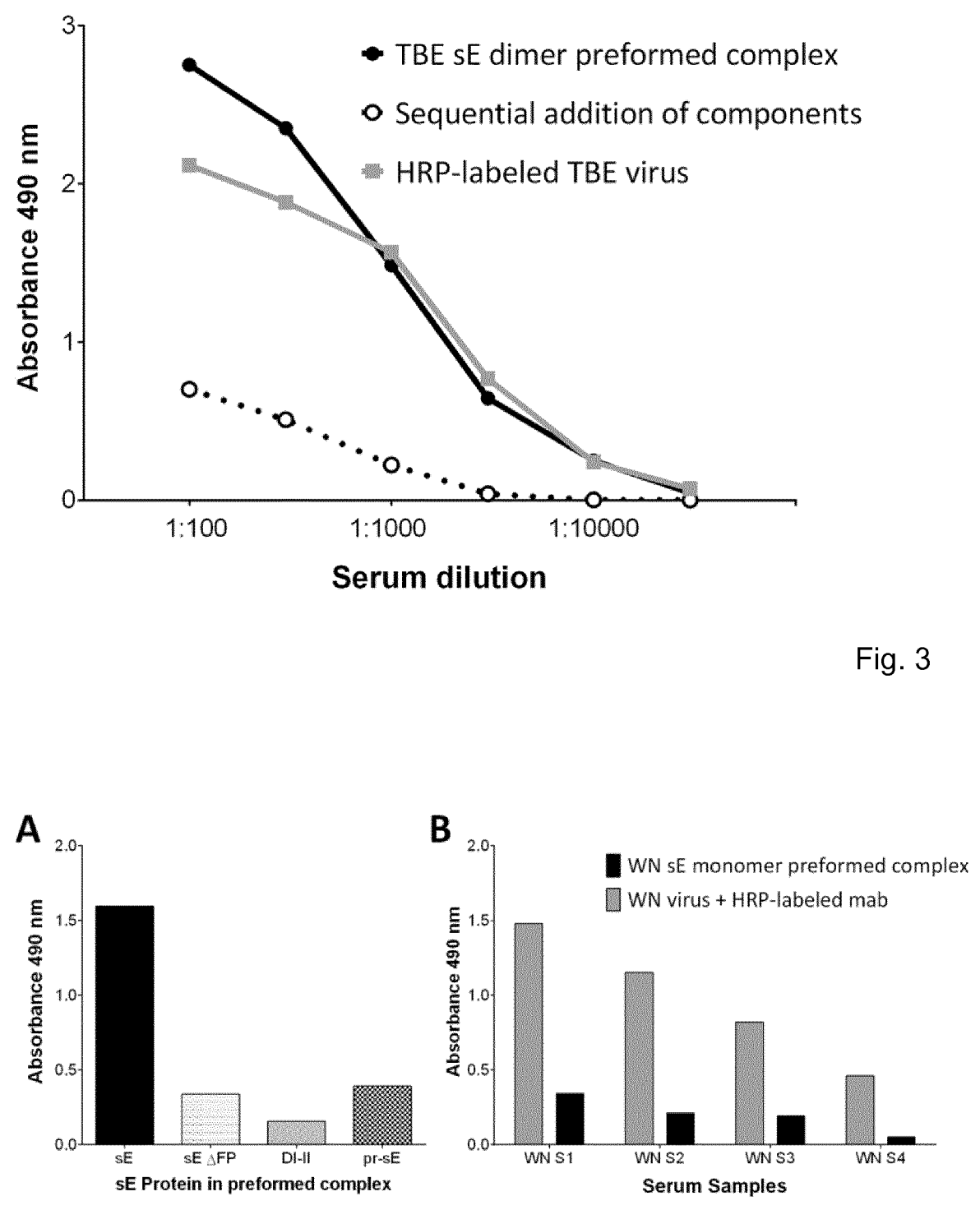
Figure 9:
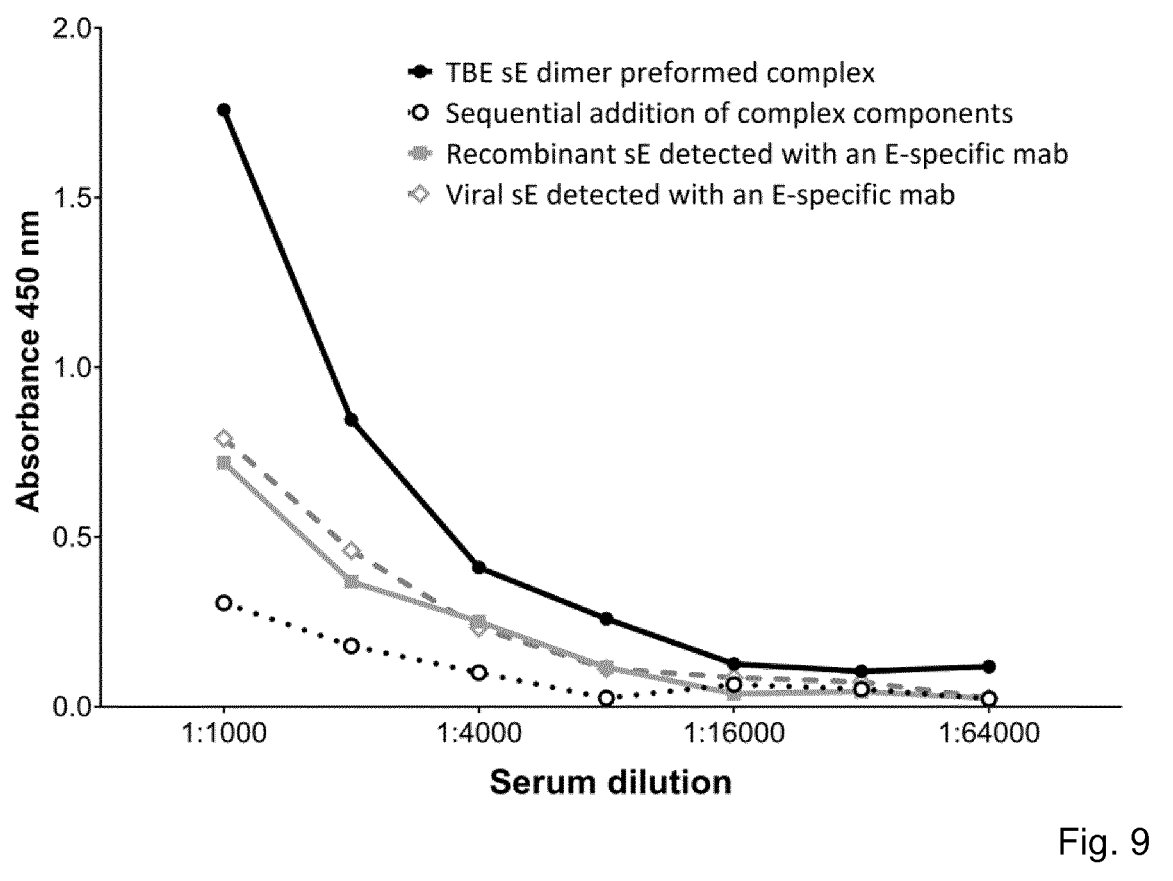

The findings that antibody populations in sera of flaviviral infected or vaccinated patients primarily consisted of IgG antibodies directed to complex epitopes of domains DI and/or DII of the flaviviral E protein (Jarmer et al., J. Virol. 88 (2014): 13845-13857; Vratskikh et al., Plos Pathogens 9 (2013): e1003458; Vogt et al. J. Virol. 83(2009): 6494-6507) set the stage for the development of improved immunization protocols and antibody detection assays. As such, WO 99/06068 A2 describes a process of immunizing mice with recombinant truncated dimeric E proteins and analysing the sera ten days after the last injection, showing the presence of IgG antibodies using recombinant truncated dimeric E proteins as antigens in an indirect ELISA as well as neutralizing antibodies (PRNTs). In contrast, the present test system provides a preformed sE dimer-marker complex in a MAC-ELISA system for the diagnosis of acute flavivirus infections. The advantages of the inventive assay manifest in the highly specific detection of flavivirus IgM antibodies in human sera for simultaneous differential diagnosis of various flaviviral infections. Although it was expected from the prior art (Van Loon et al. J. Clin. Microbiol. 13 (1981): 416-422; Van Loon et al. J. Clin. Microbiol. 17 (1983): 997-1004 and Heinz et al. J. Clin. Microbiol. 14 (1981): 141-146) that a MAC-ELISA assay could be more sensitive than an indirect ELISA, the observed technical effect due to the use of a preformed sE dimer-marker complex according to the present invention, rather than sE alone, was surprising and provides a faster and more reliable test in patients with suspected flavivirus infection (FIGS. 3 and 9).

Figure 2:
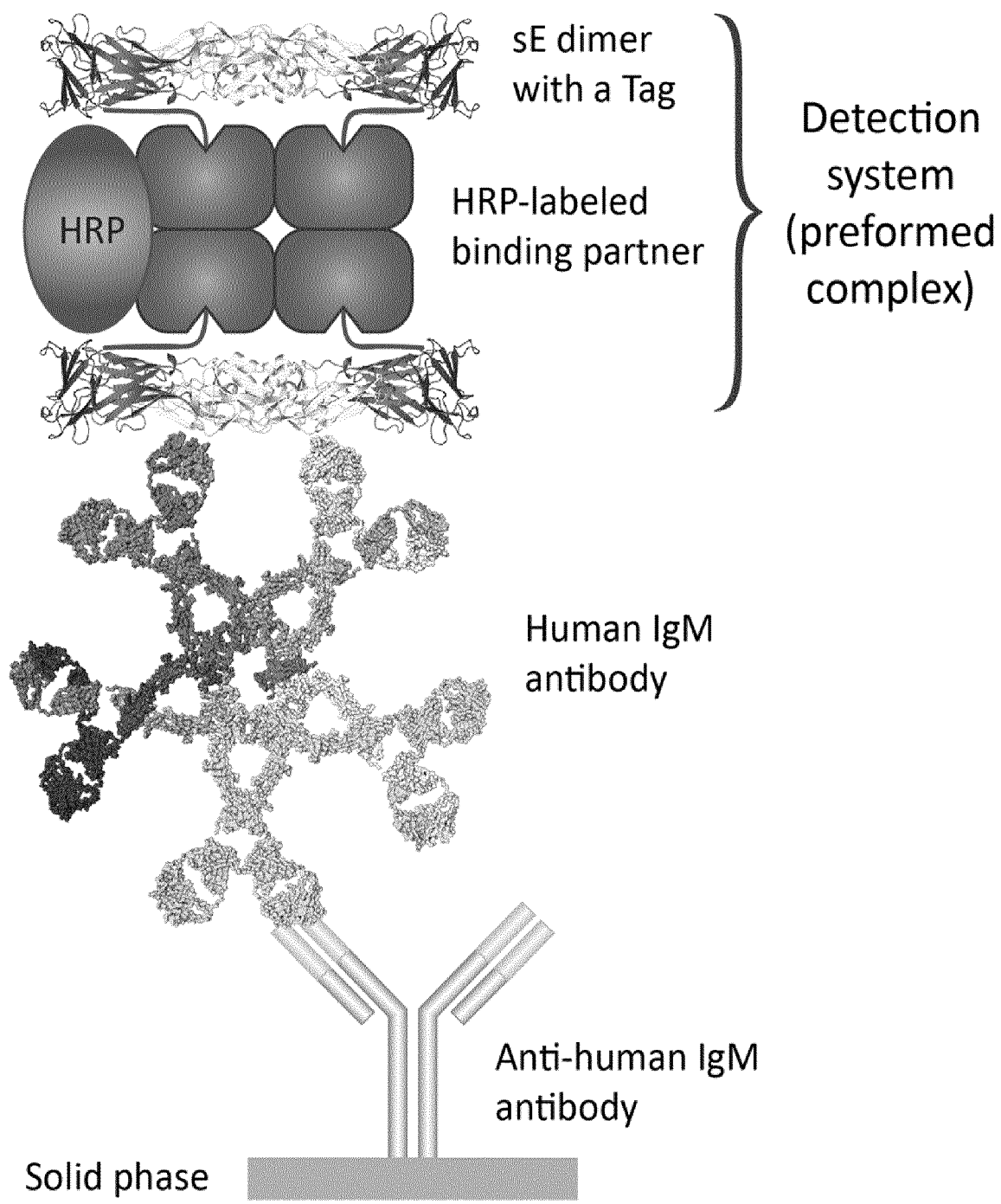

The present invention therefore provides a novel detection system, comprising the following constituents: A recombinant soluble flavivirus E protein (sE; the main component of the flavivirus surface; see FIG. 1A) provided as an antiparallel dimer (FIG. 1B). It is important for the assay of the present invention to provide the E protein as antiparallel sE dimer and not in another form (such as monomeric forms of sE or in a naturally occurring immature or mature form (e.g. in whole virus particles or VLPs)). Preferably, the sE antiparallel dimer comprises (preferably at the carboxy-terminus) a tag. Via this tag or with other complex-forming moieties, a complex with a marker (e.g. an enzyme-labelled protein) can be formed, and this preformed complex is used as a detector in the MAC-ELISA (FIG. 2). With this set-up, a highly sensitive and specific test for the detection of flavivirus IgM antibodies is provided. It is decisive for the test quality that a) the anti-parallel dimeric structure of E protein is used (FIG. 1B), and that b) a preformed complex (FIG. 2), and not of the individual components in sequential form are used (FIG. 3). Moreover, it is highly advantageous to use a tag recognizing protein with multiple binding sites to pre-form the complex to be added to the IgM antibodies of the sample captured by the immobilised IgM-binding molecules.

Figures 5, 6:
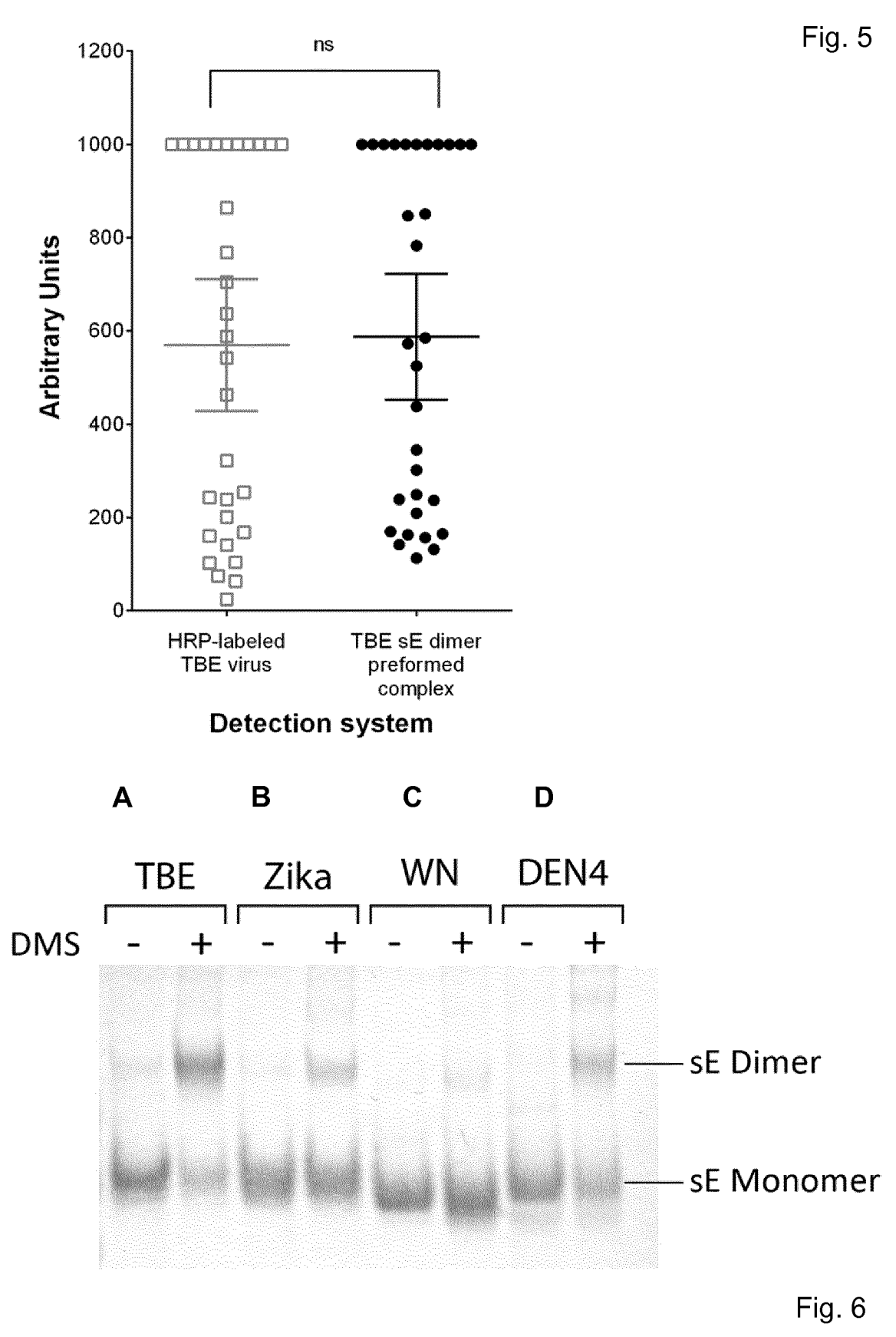

Experiments conducted in the course of the present invention (see example section below; FIGS. 3 and 4) have shown that observed technical effect of the present invention (namely a highly sensitive and specific test; FIG. 3) could not be achieved if a) recombinant E proteins are used as monomers rather than as antiparallel dimers (FIG. 4A, B) and b) the antigens are not provided as a preformed complex with the marker (e.g. the enzyme-labelled multivalent protein) but are used sequentially (dashed line in FIG. 3). On the other hand, the surprisingly advantageous performance of the method and assay system of the present invention is shown e.g. in FIG. 5 wherein the inventive assay system is compared with an established test system for TBE and in FIG. 6 wherein the performance in the diagnosis of recent infections with TBE virus (FIG. 5A), Zika virus (FIG. 5B) and dengue viruses (FIG. 5C) is illustrated. The observed technical effect of the present invention was also shown in a comparison test with conventional MAC ELISAs using dimeric forms of sE (FIG. 9). Whereas sequential addition of the soluble sE dimer and the marker (FIG. 9, black dotted line) resulted in weaker sensitivity compared to conventional MAC ELISAs (FIG. 9, grey solid and dashed lines), addition of a preformed complex comprising the soluble sE dimer and the marker according to the present invention led to a drastic increase in sensitivity, which was superior over all other formats (FIG. 9, black solid line).

Accordingly, it is essential for the method according to the present invention to add the complex comprising the antiparallel dimer of sE and the marker to the immobilised IgM antibodies rather than adding the components of the complex separately.

The provision of an antiparallel dimer of sE in the present test system is of particular relevance for the performance of the present invention. Flavivirus E proteins are well characterised and consist of an ectodomain, followed by a stem which links the ectodomain to a membrane anchor which anchors the protein in the lipid bilayer membrane. The ectodomain contains three domains, Domain I (with the N-terminus covered within the domain), Domain II and Domain III, each comprising antigenic determinants which usually do not overlap. The membrane anchor has two transmembrane segments with the C-terminus being present on the stem/ectodomain side of the membrane (see e.g. 21 (for TBE), 22 (for Dengue), 23 (for Zika)). A high number of flavivirus protein E sequences is known and available in the sequence databases, representative examples of tick-borne encephalitis virus (TBEV) are available under GenBank no. U27495; of dengue virus (DENV), especially of DENV serotype 1 (DEN1) under GenBank no. AF226687, of DENV serotype 2 (DEN2) under GenBank no. U87411, of DENV serotype 3 (DEN3) under GenBank no. DQ863638, and of DENV serotype 4 (DEN4) under GenBank no. NC_002640; and Zika virus (ZV) under GenBank no. KJ776791 (all sequence database entries referred to in the present application: according to 20 May 2016).

The sE is defined by comprising the complete ectodomain of flavivirus protein E, optionally comprising parts or whole of the stem domain and lacking the anchor domain. The sE dimer according to the present invention is defined as being "antiparallel", meaning that the dimer must be a "head-to-tail" aggregate (see e.g. FIG. 1B) in contrast to dimers with other subunit configurations.

The sE used in the present invention is—by definition—a "soluble" protein. This means that the sE is devoid of any membrane anchor. Accordingly, sE is devoid of amino acids constituting the transmembrane segment (e.g. starting at amino acid 454, 455 or 456 in TBE, 453, 454 or 455 in DEN1, 2 and 4, 451, 452 or 453 in DEN3, and 462, 463 or 464 in ZV).

The sE of the present invention may contain parts of the stem region or even the whole stem region, e.g. amino acids between amino acid 400 to 410 to amino acids 454, 455 or 456 in TBE, amino acids between amino acid 399 to 409 to amino acid 453, 454 or 455 in DEN1, 2 and 4, amino acids between amino acid 397 to 407 to amino acid 451, 452 or 453 in DEN3, amino acids between amino acid 408 to 418 to amino acid 462, 463 or 464 in ZV.

According to a preferred embodiment, the sE according to the present invention is also devoid of any stem region sequences.

The sE protein according to the present invention is provided by recombinant technology due to practical reasons. Accordingly, it is mainly or exclusively comprised by the naturally occurring flavivirus protein E sequences or combinations thereof (e.g. chimeric E proteins containing protein E sequences of two or more flaviviruses (of course, still forming antiparallel sE dimers), optionally supplemented or embedded in non-naturally occurring sequences (i.e. sequences that do not occur in native flaviviruses). It is therefore possible to include further sequences, which are not necessarily of flavivirus origin. For example, it is specifically preferred to provide a tail to the sE, preferably at the C-terminus, which may serve as a tag. The tag may be used for purification of the sE as well as for formation of the complex according to the present invention and for the detection of the sE (and the complex as a whole) after binding to the IgM antibody.

The sE sequences may also be subjected to specific changes to improve the properties of the sE, e.g. making it easier to produce, purify, handle, making it more antigenically more reactive, changing its antigenic properties, changing its binding properties to immunoglobulins, etc. Also such sE variants may be applied in the present invention, provided, of course, that the variation does not lead to the inability to form the antiparallel dimer structures needed for the present invention or deteriorates the specific IgM binding properties (or destroys the ectodomain structure).

The IgM-binding molecules are not critical for the present invention as long as they are specific enough to effectively bind IgM molecules in the sample. Preferably, the IgM binding molecules are anti-IgM antibodies or IgM-binding fragments thereof; these IgM binding molecules have already been successfully applied in prior art MAC ELISAs for flavivirus IgMs. Also other affinity binders to IgM are widely known in the art; some are antibody-derived or antibody-based, some are not. Examples of such commercially used or suggested IgM binding molecules are anti-IgM Affibody® molecules (from abcam, e.g. ab36088), C1q (U.S. Pat. No. 5,077,391 A), mannan binding protein (U.S. Pat. No. 5,112,952 A, e.g. ImmunoPure), mannose binding protein (26), unspecific IgM binding peptides (WO 98/26794 A1, EP 0 752 425 A2), specific IgM binding peptides (e.g. KAPTIN-M™ by Technogen or peptides according to WO 2001/002001 A1). Another example of a suitable IgM binding molecule is an IgM-specific Fc receptor, e.g. Fc receptor for IgM heavy chains (FcμI), in particular, Faim 3/Toso and also CD351 (Fcμ/αR), or a functional fragment thereof, which preferably comprises the Ig-like domain of Faim 3/Toso (as disclosed in WO 2016/059018 A1). The specific IgM molecule to be used in the assay may usually be selected based on the nature of the specific virus(es) to be tested, the sample and the specificity of the IgM binding molecule (for example that it allows specific discrimination between IgM and IgG; preferred IgM binding molecules are therefore molecules that exhibit a higher affinity for IgM than for IgG, i.e. that allow a selective binding of IgM from an IgG/IgM containing sample). Various technologies are available to create specific IgM binding molecules based on engineering antibody-derived scaffolds and shuffling antibody-derived binding sequences.

The method according to the present invention is particularly suitable to detect specific IgMs for tick-borne encephalitis virus (TBEV), dengue virus (DENV), especially DENV serotype 1 (DEN1), DENV serotype 2 (DEN2), DENV serotype 3 (DEN3), and DENV serotype 4 (DEN4), and Zika virus (ZV).

The method according to the present invention is preferably performed on samples known to potentially contain flavivirus specific IgMs. Accordingly, preferred samples are all possible sample derived from blood (samples derived from human blood), especially serum or plasma samples, and cerebrospinal fluid (CSF) samples.

A particularly preferred embodiment of the present invention uses an sE molecule with a tag that binds to the marker. Accordingly, the antiparallel dimer of sE preferably comprises a tag and wherein the tag links the marker to the antiparallel dimer of sE. Examples for suitable tags are e.g. reviewed in reference 24 or 25 and include poly-His, Glutathione S-Transferase, maltose binding protein, calmodulin binding peptide, intein-chitin binding domain, Streptavidin/Biotin based tags, His-Patch ThioFusion, tandem affinity tags, peptide/epitope tags, reporter tags, beta-Galactosidase, alkaline phosphatase, chloramphenicol acetyl transferase, horseradish peroxidase, ubiquitine modifiers, HaloTags®, Profinity eXact™, PDZ domain-based tags, FLAG, c-Myc, GM-CSF, Twin StrepII, MBP, GST, starch, fluoroapetite, diatomite, beta-GRP, ELP, RTX, ELK16, Fh8, 4AaCter, PagP, eGFP, heme, PYP, NusA, SUMO, Trx, XTEN, FATT, etc (s. 24, 25). In a preferred embodiment, the tag is a Strep-tag, or a His-tag.

In the present method, all suitable markers can be applied which are able to be provided in a complex with the antiparallel dimer of sE. Preferably, all markers that have been established in MAC ELISAs are suitable, especially those that have already been applied in flavivirus MAC ELISAs. Accordingly, preferred markers are selected from the group consisting of an affinity marker, a fluorescence marker, a radioactive marker, a nucleic acid marker, a chromogenic marker, a luminescence marker, a magnetic marker, or combinations thereof. For example, the marker may be selected from a chromogen, an enzyme, a catalyst, a fluorophore, a gold colloid and a direct visual label. In the case of a direct visual label, use may be made of a colloidal metallic or non-metallic particle, a dye particle, an enzyme or a substrate, an organic polymer, or a latex particle. A large number of enzymes suitable for use as labels are disclosed in e.g. U.S. Pat. Nos. 4,366,241 A; 4,843,000 A and 4,849,338 A. Suitable enzyme labels in the present invention include alkaline phosphatase, horseradish peroxidase, preferably horseradish peroxidase. The enzyme label may be used alone or in combination with a second enzyme, which is in solution. In the present invention a secondary antibody attached with horseradish peroxidase, which then reacts with its substrate DAB and produces a visually detectable colour change, preferably achieves the detection of the complex. Other labelling methods, like biotinylation or labelling with a fluorescent moiety such as FITC, PE or a fluorescent protein, may also be used. Also a second, a labelled antibody, preferably monoclonal, may then be used to detect and quantify the immune complexes. If the label is biotin, detection may be performed by adding an avidin- or streptavidin-labelled enzyme in a further step. Addition of a substrate of the enzyme, as well-known in the state of the art, allows for quantification of label, and consequently, of antibody in immune complexed form.

In a preferred embodiment, the complex used in the method according to the present invention comprises a labelled antibody, especially an antibody being specific for a tag of the antiparallel dimer of sE; a Strep-tag binding protein, especially a Strep-tag binding protein comprising a marker as mentioned above.

The solid support used in the present method may be any suitable solid support allowing (1) binding of the IgM binding molecules and (2) binding of the IgM in the sample to the IgM binding molecules bound to the solid surface. The solid support should also allow proper handling of the immobilised sample IgMs in the binding to the complex and the detection of the binding event of the complex to the immobilised IgM. The solid support is therefore preferably a material that is already used in ELISAs, especially in MAC ELISAs. Preferred solid supports are therefore a microtiter plate, a biological microchip, a bead, a disc, a magnetic particle or other plastic containers or surfaces, a fiber optic sensor, a glass slide, or a membrane, preferably a nitrocellulose membrane, a polytetrafluorethylene membrane, a cellulose acetate membrane or a cellulose nitrate membrane. Preferably, the method according to the present invention is performed in an automated system. Accordingly, all solid supports that are established or suitable for automated detection systems may be applied in the method according to the present invention. For example, the method and test set-up according to the present invention can readily be adapted to already existing, commercially available automated systems, such as Architect Immunoassay Analyzer (Abbott); Vidas Immunoanalyzer (Biomerieux); Cobas and Elecsys automated Immunoassay-Analyzers (Roche Diagnostics); Liaision Analyzer (Diasorin); Euroimmun Analyzers (Euroimmun), etc.

Depending on the nature of the marker, it may be necessary in the present method to add further substances to finally detect the marker. The addition of further substances thereby generates a signal or activates the marker thereby creating a detectable signal (or creating another marker which is then subject to the creation of a signal). This signal may then be finally detected and measured to detect and eventually also quantify the amount of IgM antibodies specific for flavivirus bound to the IgM binding molecules on the solid surface. This allows then the conclusion whether or not (and if yes, in which amount) flavivirus specific IgMs have been contained in the sample. This is then indicative whether the person from which this sample was taken was affected by a flavivirus infection.

With the present assay set-up it is also possible to discriminate between different flavivirus infections and even discriminate between the dengue serotypes and detect multiple infection with different flaviviruses.

According to a preferred embodiment of the present invention, the method applies sE of a flavivirus distantly related to the important human pathogenic flaviviruses (such as Rio Bravo, Modoc, Yokose, Entebbe bat, Barkedji, Lammi viruses) as a control for determining broadly flavivirus cross-reactive antibodies. A specifically preferred example for such control sE is sE of Rio Bravo virus. Using such an sE can be advantageous to optimise the method according to the present invention for controlling the specific background of broadly cross-reactive antibodies. The term "broadly (flavivirus) cross-reactive antibodies" relates to antibodies that are cross-reactive to all or most of the flaviviruses and distinguishes from "serocomplex-cross-reactive antibodies", such as the antibodies that are cross-reactive e.g. between the dengue serotypes. With Rio Bravo virus sE, not only unspecific background can be determined (and subtracted from the overall results) but also the specific background of broadly flavivirus cross-reactive antibodies.

According to another aspect, the present invention relates to a kit suitable for performing the method according to the present invention. This kit according to the present invention comprises:
- a solid support comprising immobilised IgM-binding molecules and
- a complex comprising
  (i) an antiparallel dimer of soluble flavivirus Protein E (sE) and
  (ii) a marker.

The kit according to the present invention may preferably further comprise means to detect the marker, preferably means for detecting an affinity marker, a fluorescence marker, a radioactive marker, a chromogenic marker, a luminescence marker, or a magnetic marker.

Preferably, the kit of the present invention, further comprises a sample or a container containing a sample and/or a standard comprising IgM antibodies specific for a flavivirus.

As already stated above, it is advantageous to perform the present method with sE from Rio Bravo virus or another flavivirus distantly related to the important human pathogenic flaviviruses for determining the specific background of broadly flavivirus cross-reactive antibodies. Accordingly, the kit according to the present invention preferably comprises such sEs or the complex comprising such sEs.

The method according to the present invention is preferably performed as an automated system. Accordingly, the kit according to the present invention preferably also comprises components that are necessary or helpful in conducting such automated detection. According to a preferred embodiment, the present kit further comprises an automated detection system, preferably comprising a sample conveying device, a detection device, a computer processing unit and/or a display for displaying the signal from the detection unit processed by computer software programs executed with the computer processing unit.

Specifically preferred components of such an automated system are those that are already part of commercially available automated systems, such as the Architect Immunoassay Analyzer (Abbott); Vidas Immunoanalyzer (Biomerieux); Cobas and Elecsys automated Immunoassay-Analyzers (Roche Diagnostics); Liaision Analyzer (Diasorin); Euroimmun Analyzers (Euroimmun), etc. referred to above.

The kit may be provided in a commercial set-up as a ready to use kit. Preferably, the components of the kit are packed in a sterile wrap, preferably in a sterile transparent plastic wrap. The components may be pre-sterilised, provided by means of sterile production or may be sterilised at the end of the production process, i.e. even after wrapping the components of the kit for final packaging. The kit may be accompanied by suitable product leaflets with instructions for use and finally provides in a product box (e.g. a sealed product box) for sale. If the kit is marketed as an automated system, usually not the whole system needs to be sterile wrapped. Accordingly, it is preferred to provide at least the solid support and/or the complex and/or the sE and the marker packed in a sterile wrap, preferably in a sterile transparent plastic wrap.

The present invention is further disclosed by the following examples and the figures, yet without being restricted thereto.

FIG. 1: Illustration of antigens used in the present invention; A: Schematic representation of a flavivirus particle in immature (left) and mature (right) form. Viral proteins: E—envelope; prM—precursor of membrane protein; M—membrane protein; C—capsid protein; sE—C-terminally truncated soluble form of E lacking the so-called "stem" and the transmembrane anchor. B: Ribbon diagram of the crystal structure of tick-borne encephalitis (TBE) virus sE. Upper panel: top view (showing the antiparallel dimeric structure of this protein); lower panel: side view. Color coding of the three sE domains: Domain I (DI)—red; domain II (DII)—yellow; domain III (DIII)—blue. Color coding of the three sE domains: Domain I (DI)—grey; domain II (DII)—light grey; domain III (DIII)—dark grey. C: Ribbon diagrams of monomeric soluble forms of E in their side views ($1^{st}$ panel: sE monomer (TBE); $2^{nd}$ panel: sEΔFP (TBE sE monomer in which amino acids 98 to 111 were replaced by a GGGG-linker); $3_{rd}$ panel: DI+DII monomer (TBE); $4^{th}$ panel: pr+sE monomer (DEN2), FP—fusion peptide).

FIG. 2: Schematic representation of the test principle in the present invention; MAC (IgM antibody capture) ELISA format used in the invention; HRP—horseradish peroxidase.

FIG. 3: Titration curves of a serum pool of recent human TBE virus infections in three different MAC ELISAs. Black solid line: Assay according to the invention. Grey solid line: Conventional assay according to references (4), (17). Black dotted line: Assay according to the invention but using sequential addition of the detector components.

FIG. 4: MAC ELISAs using monomeric and dimeric E antigens in the detector complex. A: A 1:100 dilution of a serum pool of recent human TBE virus infections was analyzed in the inventive assay using the TBE sE dimer (black column), TBE sE ΔFP, TBE DI+II and TBE pr-sE (grey-shaded columns) as antigens in the detector complex. B: Four serum samples from recent human WN virus infections were analyzed at a dilution of 1:100 in the inventive assay format using the monomeric WN sE in the detector complex (black columns) in comparison to a MAC ELISA using purified whole WN virus particles as an antigen (grey columns). HRP—horseradish peroxidase; mab—monoclonal antibody FIG. 5: Results of TBE IgM determinations of 31 human serum samples from recent TBE virus infections in the inventive assay (black dots) compared to the conventional MAC ELISA using purified infectious TBE virus (open squares), expressed in arbitrary units. Ns—not significant. The bars indicate the mean+/− 95% confidence intervals. Serum dilution—1:1000.

FIG. 6: Demonstration of the oligomeric structure of recombinant sE proteins from TBE, Zika, WN, and DEN4 viruses. SDS-PAGE of recombinant sE proteins without (−) and after chemical cross-linking with DMS (+). Staining with Coomassie Blue.

FIG. 7: Results of the analysis of serum samples of recent flavivirus infections using the inventive assay with a panel of flavivirus sE antigens as indicated on the x-axis. A: TBE virus infection; B: Zika virus infection; C: Dengue 2 virus infection; D: Dengue 3 virus infection; E: Zika and Dengue 2 virus double infections; F: Dengue 3 virus infection. Serum dilution—1:100.

FIG. 8: Results of the analysis of serum samples of recent dengue infections using the inventive assay with dengue serotype 1 to 4 sE antigens as indicated on the x-axis. A: Dengue 1 virus infection; B: Dengue 2 virus infection; C: Dengue 3 virus infection; D: Dengue 4 virus infection. Serum dilution—1:100.

FIG. 9: Titration curves of a serum pool of recent human TBE virus infections in four different MAC ELISAs. Black solid line: Assay according to the invention. Black dotted line: Assay according to the invention but using sequential addition of the detector components. Grey solid line: Conventional TBE MAC ELISA, using the same recombinant, strep-tagged sE as in the inventive complex, but a Biotin-labeled E-protein specific monoclonal antibody (mab) and streptavidin-HRP for detection. Grey dashed line: Conventional TBE MAC ELISA, using an untagged sE dimer (isolated form purified TBE virus, Heinz et al. 1991, J Virol 65 (10):5579-5583), and a Biotin-labeled E-protein specific monoclonal antibody (mab) and streptavidin-HRP for detection.

EXAMPLES

Abbreviations

DI, II, III domain I, II, III
DEN dengue
DMS dimethyl suberimidate
ELISA enzyme linked immunosorbent assay
FP fusion peptide
HRP horseradish peroxidase
JE Japanese encephalitis
MAC ELISA IgM antibody capture ELISA
PBS phosphate buffered saline
RB Rio Bravo
SDS-PAGE sodium dodecyl sulfate polyacrylamide gel electrophoresis
sE soluble E
TBE tick-borne encephalitis
WN West Nile
Materials and Methods
Human Serum Samples.

Serum samples of patients were sent to the Department of Virology, Medical University of Vienna, and stored at −20° C.

Virus Production and Inactivation.

Virus production was carried out essentially as described in references (3, 19). In brief, primary chicken embryo cells were infected with TBE virus, strain Neudörfl (GenBank # U27495) or WN virus, strain NY99 (GenBank # AF196835). 24-48 hours p.i. the cell supernatant was harvested and clarified by centrifugation. WN virus was inactivated with formalin (1:2000) for 24 h at 37° C. Virus-containing suspensions were concentrated by ultracentrifugation and purified by rate zonal followed by equilibrium sucrose density gradient centrifugation.

Production of Recombinant E Proteins.

The recombinant antigens were produced in the Drosophila Expression System (Invitrogen) with a double strep-tag as described in references (5, 18-20). The expression vector pT389 encodes the export signal sequence Bip, an enterokinase cleavage site and the double strep-tag. Drosophila Schneider 2 cells were stably transfected using blasticidin for selection. Protein expression was induced by the addition of $CuSO_4$ and supernatants were harvested 7-10 days after induction. Antigens were purified via affinity chromatography with Streptactin columns (IBA) according to the manufacturer's instructions.

The following recombinant proteins were expressed and used as antigens in the inventive MAC-ELISA:

TBE virus: sE—amino acids E 1 to 400; TBE virus DI+II—amino acids E 1 to 302; TBE virus sE ΔFP—amino acids 1 to 400 (amino acids 98-111 were replaced by a GGGG-linker); TBE virus pr+sE [amino acids sE 1 to 400; prM 1 to 129 with a mutation in the furin cleavage site as described in reference (2); prM and sE were connected by the tobacco etch virus protease cleavage site as described in reference (7)]

WN virus: sE—amino acids E 1 to 400; DEN viruses: sE—amino acids E 1 to 399 for DENV1, 2 and 4; 1 to 397 for DENV3; Zika virus: sE—amino acids E 1 to 408; Rio Bravo: sE—amino acids E 1 to 395
TBE (Neudörfl); GenBank # U27495
WN (NY99); GenBank # AF196835
Dengue 1 (FGA/89); GenBank # AF226687
Dengue 2 (16681); GenBank # U87411
Dengue 3 (CH53489); GenBank # DQ863638
Dengue 4 (11070); GenBank # NC_002640
Zika (H/PF/2013); GenBank # KJ776791
Rio Bravo (RiMAR); GenBank # AF144692
Labeling of Virus and Mab.

Purified infectious TBE virus and the WN specific monoclonal antibody were labeled with horseradish peroxidase (HRP) using the "Lightning link HRP labeling kit" (Innova Biosciences) according to the manufacturer's instructions.

Chemical Cross-Linking and SDS-PAGE

Chemical cross-linking of recombinant proteins was performed essentially as described previously (1). Briefly, 10 mM dimethyl suberimidate (DMS; Pierce) was added to the recombinant proteins in triethanolamine buffer pH 8.0 and incubated for 30 minutes at room temperature. Cross-linking was stopped by the addition of ethanolamine to a final concentration of 10 mM. Proteins were precipitated with trichloroacetic acid, subjected to SDS-PAGE using 5% polyacrylamide gels under non-reducing conditions as described in reference (9) and stained with Coomassie blue R-250.

MAC ELISA

For all MAC ELISA formats Nunc MaxiSorp plates were coated overnight at 4° C. with 50 µl/well of rabbit immunoglobulin against human µ chains (DAKO) diluted 1:1,000 in carbonate buffer (pH 9.6; 0.159% $Na_2CO_3$ and 0.293% $NaHCO_3$). After removal of the coating solution serum samples in PBS (phosphate buffered saline) buffer pH 7.4 (containing 2% Tween 20 and 2% sheep serum) were added and incubated for 45 minutes at 37° C.

Serum samples were then removed and after three washing steps with PBS pH 7.4 different detection systems were applied as follows:

a) Conventional TBE MAC ELISA (4, 17): Peroxidase-labeled infectious TBE virus was incubated for 30 minutes at 37° C.
b) Conventional WN MAC ELISA: Formalin-inactivated WN virus was incubated for 30 minutes at 37° C. followed by a 30-minutes incubation with a WN virus specific peroxidase-labeled monoclonal antibody.
c) Preformed inventive complex: sE proteins and Streptactin-HRP (IBA) were mixed in pre-determined optimal concentrations, incubated for 30 minutes at 500 rpm at room temperature and either stored at −80° C. or directly used. The complex was incubated for 30 minutes at 37° C.
d) Sequential addition of the components of the inventive complex in the same concentrations as used in the complex: sE was incubated for 30 minutes at 37° C. followed by a 30-minutes incubation with Streptactin-HRP.
e) Conventional TBE MAC ELISA, using the same recombinant, strep-tagged sE as in the inventive complex, but a Biotin-labeled E-protein specific monoclonal antibody (mab) and streptavidin-HRP for detection: sE was incubated for 30 minutes at 37° C. followed by a 30-minute incubation with the mab and a 30-minutes incubation with the streptavidin-HRP.

f) Conventional TBE MAC ELISA, using an untagged sE dimer (isolated form purified TBE virus, Heinz 1991), and a Biotin-labeled E-protein specific monoclonal antibody (mab) and streptavidin-HRP for detection: sE was incubated for 30 minutes at 37° C. followed by a 30-minutes incubation with the mab and a 30-minutes incubation with the streptavidin-HRP.

Then the plates were washed three times and 50 µl substrate (o-phenylenediamine; Sigma) were added. The enzyme was allowed to react for 30 minutes at room temperature in the dark and stopped by the addition of 100 µl 2N $H_2SO_4$.

Results

Demonstration that 1.) the MAC ELISA according to the invention is equivalent to a MAC ELISA in which HRP-labeled infectious TBE virus is used for detection and that 2.) this performance is only achieved when the detector components are added as a preformed complex and not when the individual components are added sequentially.

In order to assess the quality of the assay according to the invention, we compared its performance with a) that of an established MAC ELISA that uses purified infectious HRP-labeled tick-borne encephalitis (TBE) virus as detector (4, 17) and b) an assay format in which the individual components of the inventive detector complex were added sequentially. As can be seen in FIG. 3, the sensitivity of IgM detection with the inventive assay in a pool of serum samples from recent TBE virus infections was equivalent to the conventional assay. In contrast, a much lower signal was obtained when the individual detector components (sE dimer and HRP-streptactin) were added sequentially (FIG. 3).

FIG. 3 shows titration curves of a serum pool of recent human TBE virus infections in three different MAC ELISAs (Black solid line: Assay according to the invention; Grey solid line: Conventional assay according to references (4, 17); Black dotted line: Assay according to the invention but using sequential addition of the detector components.

Demonstration that the excellent performance of the MAC ELISA according to the invention is dependent on the anti-parallel dimeric structure of sE used in the detector complex.

For analyzing the structural requirements of the antigen used in the detector complex, we compared the TBE virus sE dimer with different monomeric forms of this protein. This included 1.) sE in which a sequence element required for dimerization (amino acids 98 to 111, fusion peptide FP) in domain II was removed (sE ΔFP), 2.) a construct comprised only of domains I+II (DI+II) and 3.) a monomeric sE in complex with pr (pr+sE).

The results in FIG. 4A show that the performance of the assays with the monomeric forms (grey-shaded columns, FIG. 4A) is dramatically reduced compared to the inventive assay using dimeric sE (black column, FIG. 4A).

In addition, we analyzed the inventive assay format in another flavivirus system [West Nile (WN) virus] which like Japanese encephalitis (JE) virus—in contrast to TBE and other flaviviruses (5, 8, 10, 11, 15)—yields a monomeric form of sE upon production as a recombinant protein (6, 8, 13). Consistent with the results obtained with the monomeric TBE sE forms (FIG. 4A), very low signals were observed with the monomeric WN virus sE compared to a MAC ELISA using purified whole virus particles (FIG. 4B).

These results demonstrate that the quality of the inventive assay is dependent on the native antiparallel structure of the flavivirus E antigen in the detector complex.

FIG. 4 shows MAC ELISAs using monomeric and dimeric E antigens in the detector complex (A: A 1:100 dilution of a serum pool of recent human TBE virus infections was analyzed in the inventive assay using the TBE sE dimer (black column), TBE sE ΔFP, TBE DI+II and TBE pr-sE (grey-shaded columns) as antigens in the detector complex; B: Four serum samples from recent human WN virus infections were analyzed at a dilution of 1:100 in the inventive assay format using the monomeric WN sE in the detector complex (black columns) in comparison to a MAC ELISA using purified whole WN virus particles as an antigen (grey columns); HRP—horseradish peroxidase; mab—monoclonal antibody).

Demonstration that the MAC ELISA according to the invention is equivalent to the conventional format using a panel of 31 human serum samples from recent TBE virus infections.

To compare the sensitivity of the inventive assay format with that of a conventional MAC ELISA using purified infectious TBE virus, we analyzed a panel of 31 serum samples from recent human TBE virus infections in both assays, using a positive standard serum for determining arbitrary TBE IgM units as described (17). The evaluation of the results revealed no statistically significant difference and complete equivalence of both assays (FIG. 5).

FIG. 5 shows the results of TBE IgM determinations of 31 human serum samples from recent TBE virus infections in the inventive assay (black dots) compared to the conventional MAC ELISA using purified infectious TBE virus (open squares), expressed in arbitrary units (Ns—not significant. The bars indicate the mean+/− 95% confidence intervals. Serum dilution—1:1000).

Demonstration that the MAC ELISA according to the invention also works for other important human-pathogenic flaviviruses that yield dimeric recombinant sE proteins and allows the sero-diagnosis of recent human TBE, dengue and Zika virus infections with high specificity.

Figure 7:
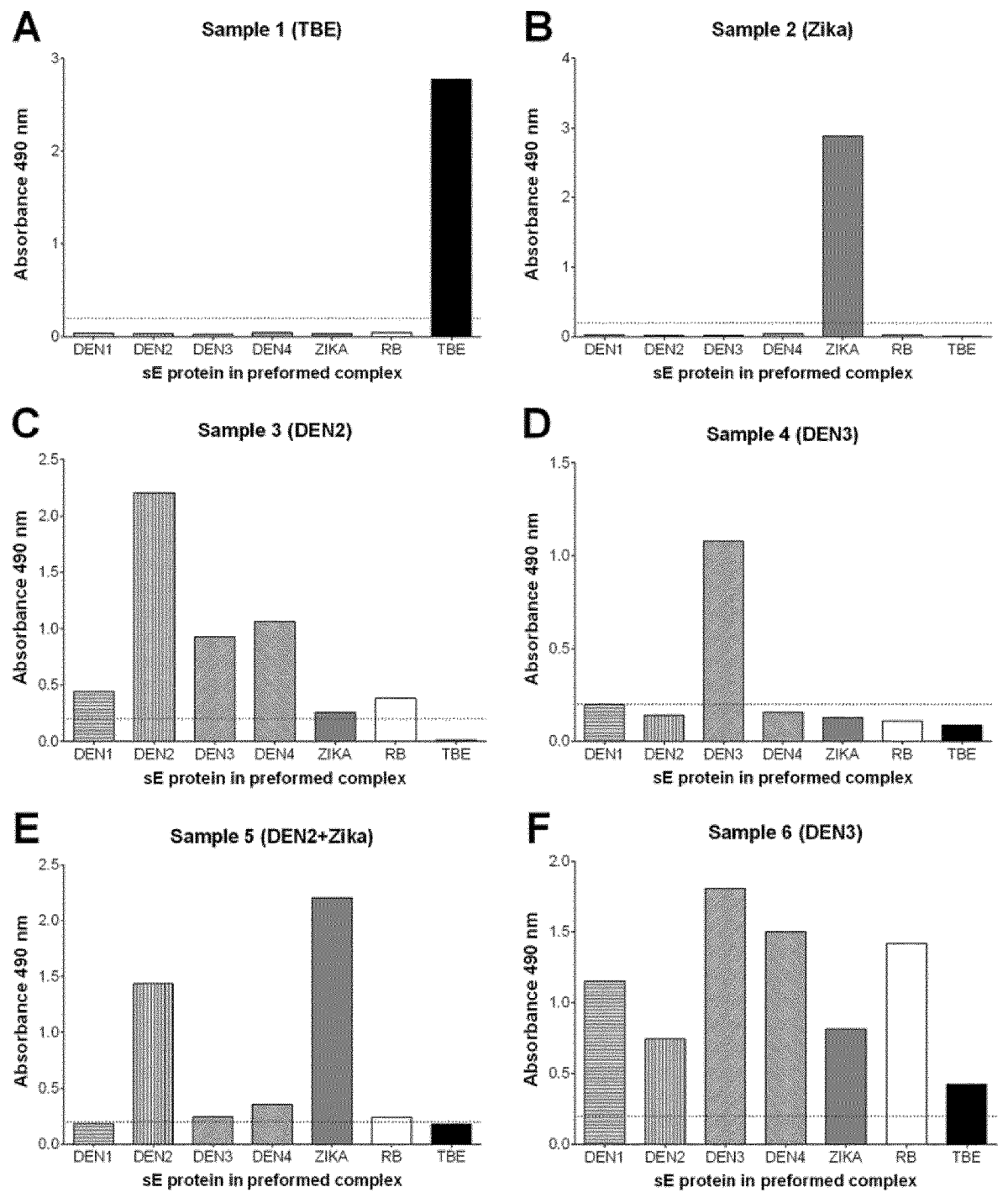

The invention is dependent on the use of the native antiparallel structure of sE. The formation of such dimers upon recombinant protein expression differs between flaviviruses, specifically the recombinant sE proteins of JE and WN are monomeric (6, 8, 13); compare FIG. 1). However, sE proteins of other important human-pathogenic flaviviruses can potentially form dimers (FIG. 6) and could thus be used directly in the inventive assay format (FIG. 7).

For this purpose, we expressed and purified recombinant sE proteins of dengue (DEN) and Zika viruses and analyzed their oligomeric structure by cross-linking with DMS in comparison to the sE proteins of TBE (predominantly dimeric) and WN (predominantly monomeric) viruses. As can be seen in FIG. 6, both DEN4 and Zika sE proteins yielded cross-linking patterns consistent with a dimeric structure, similar to TBE virus. The results obtained with DEN serotypes 1, 2 and 3 sE proteins were similar to that of DEN4.

FIG. 6 demonstrates the oligomeric structure of recombinant sE proteins from TBE, Zika, WN, and DEN4 viruses (SDS-PAGE of recombinant sE proteins without (−) and after chemical cross-linking with DMS (+). Staining with Coomassie Blue).

To demonstrate the suitability of DEN and Zika virus sE antigens for the inventive assay, we analyzed human serum samples from recent infections with these viruses in parallel with sEs of TBE, DEN serotypes 1 to 4, Zika and Rio Bravo viruses. The latter sE is used as a cross-reactive control antigen that is distantly related to all relevant human-pathogenic flaviviruses (16) and allows the determination of the contribution of broadly flavivirus cross-reactive antibodies to the assay signal. Examples of results obtained with such serum samples in inventive MAC ELISAs using Dengue serotype 1,2,3,4; Zika; Rio Bravo and TBE sE as antigens are shown in FIG. 7. The data reveal the excellent performance of the assay, allowing a type-specific serological diagnosis of important flavivirus infections of humans. Panel E shows that even recent double infections with dengue and Zika viruses can be resolved.

Sequential infections with different DEN serotypes are especially prone to the development of broadly flavivirus cross-reactive antibodies that can pose problems in the sero-diagnosis of such infections (12, 14). Including an independent flavivirus antigen that does not play a role as human pathogen (sE from Rio Bravo virus) allows the detection of the background cross-reactive fraction and can thus help to identify the recently infecting DEN virus by comparing the extents of signals in assays with all four serotypes (FIG. 7F).

FIG. 7 shows the results of the analysis of serum samples of recent flavivirus infections using the inventive assay with a panel of flavivirus sE antigens as indicated on the x-axis (A: TBE virus infection; B: Zika virus infection; C: Dengue 2 virus infection; D: Dengue 3 virus infection; E: Zika and Dengue 2 virus infections; F: Dengue 3 virus infection; serum dilution—1:100).

Figure 8:
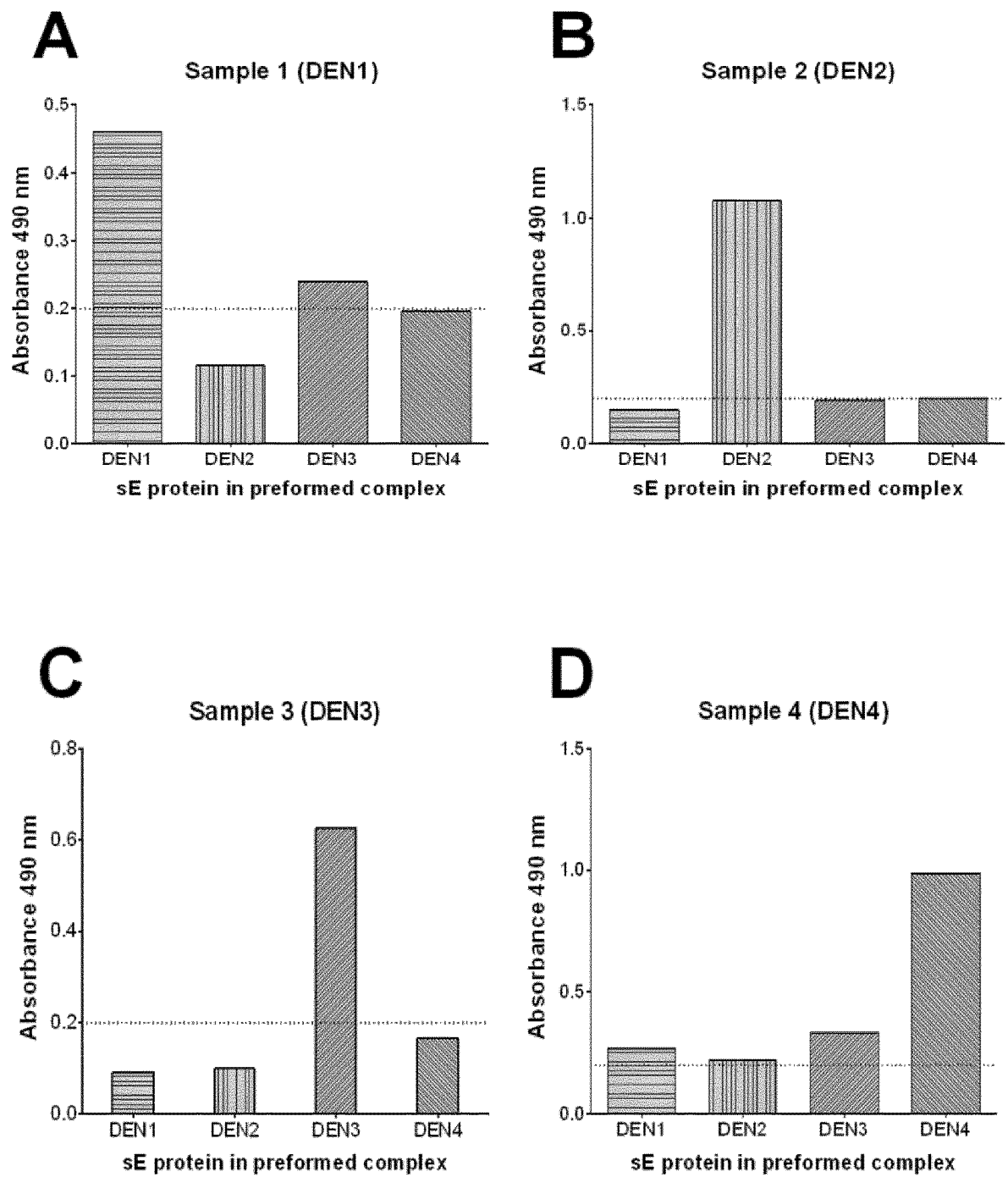

Further examples for the serotype-specific diagnosis of dengue virus infections using the inventive assay are shown in FIG. 8.

FIG. 8 shows the results of the analysis of serum samples of recent dengue infections using the inventive assay with dengue serotype 1 to 4 sE antigens as indicated on the x-axis (A: Dengue 1 virus infection; B: Dengue 2 virus infection; C: Dengue 3 virus infection; D: Dengue 4 virus infection; serum dilution—1:100).

Demonstration that the MAC ELISA according to the invention is superior compared to conventional MAC ELISA formats that also use dimeric forms of sE In order to demonstrate the improved technical effect of the inventive assay, we compared its performance with a) that of the assay according to the invention but using sequential addition of the detector components, b) a conventional TBE MAC ELISA using the same recombinant, strep-tagged sE as in the inventive complex, but a Biotin-labeled E-protein specific monoclonal antibody (mab) and streptavidin-HRP for detection and c) a conventional TBE MAC ELISA, using an untagged sE dimer (isolated from purified TBE virus, Heinz 1991), and a Biotin-labeled E-protein specific monoclonal antibody (mab) and streptavidin-HRP for detection. As can be seen in FIG. 9, the sensitivity of IgM detection with the inventive assay in a pool of serum samples from recent human TBE virus infections is surprisingly more sensitive than detection with similar methods described in the art.

The results in FIG. 9 show that adding the detector components as a preformed complex according to the invention (FIG. 9 black solid line) drastically increases the performance in comparison to sequential addition of the detector components (FIG. 9 black dotted line). In addition, the results demonstrate that with conventional MAC ELISAs using the same recombinant sE antigen (FIG. 9 grey solid line) the performance of IgM detection was much lower compared to the assay according to the invention. Same results were obtained with conventional MAC ELISAs using untagged sE dimers isolated from TBE virus (FIG. 9 grey dashed line).

The data therefore reveal that the present invention provides a highly sensitive IgM detection assay whose performance could be dramatically improved over existing conventional MAC ELISAs using sE dimers.

In view of this disclosure, the present invention provides the following preferred embodiments:

1. A method for the detection of an IgM antibody specific for a flavivirus in a sample, comprising the steps of
   (a) contacting the sample with a solid support comprising immobilised IgM-binding molecules,
   (b) allowing binding IgM antibodies in the sample to the IgM binding molecules on the solid support so that the IgM antibodies are also immobilised on the solid support, and
   (c) detecting IgM antibodies specific for a flavivirus by allowing binding of a complex comprising
      (i) an antiparallel dimer of soluble flavivirus Protein E (sE) and
      (ii) a marker
   and identifying the binding of the complex to the specific flavivirus IgM antibody by detecting the marker.

2. Method according to embodiment 1, wherein the IgM-binding molecules are anti-IgM antibodies or IgM-binding fragments thereof.

3. Method according to embodiment 1 or 2 wherein the flavivirus is selected from group tick-borne encephalitis virus (TBEV), dengue virus (DENV), especially DENV serotype 1 (DEN1), DENV serotype 2 (DEN2), DENV serotype 3 (DEN3), and DENV serotype 4 (DEN4), and Zika virus (ZV).

4. Method according to any one of embodiments 1 to 3, wherein the sample is a serum or plasma sample, or a cerebrospinal fluid (CSF) sample.

5. Method according to any one of embodiments 1 to 4, wherein the antiparallel dimer of sE comprises a tag and wherein the tag links the marker to the antiparallel dimer of sE, the tag being preferably selected from Strep-tag or His-tag.

6. Method according to any one of embodiments 1 to 5, wherein the marker is selected from an affinity marker, a fluorescence marker, a radioactive marker, a nucleic acid marker, a chromogenic marker, a luminescence marker, a magnetic marker, or combinations thereof.

7. Method according to any one of embodiments 1 to 6, wherein the complex comprises a labelled antibody, especially an antibody being specific for a tag of the antiparallel dimer of sE; a Strep-tag binding protein, especially a Strep-tag binding protein comprising a marker according to embodiment 6.

8. Method according to any one of embodiments 1 to 7, wherein the solid support is a microtiter plate or other plastic containers or surfaces, a biological microchip, a bead, a disc, a magnetic particle, a fiber optic sensor, a glass slide, or a membrane, preferably a nitrocellulose membrane, a polytetrafluorethylene membrane, a cellulose acetate membrane or a cellulose nitrate membrane.

9. Method according to any one of embodiments 1 to 8, wherein detecting the marker comprises the addition of further substances thereby generating a signal or activating the marker to elicit a signal and measuring the signal.

10. Method according to any one of embodiments 1 to 9, wherein sE of a flavivirus distantly related to the important human pathogenic flaviviruses, preferably sE of Rio Bravo, Modoc, Yokose, Entebbe bat, Barkedji, or Lammi viruses, especially sE of Rio Bravo, is applied as a control.

11. Method according to any one of embodiments 1 to 10, wherein the method is performed in an automated system.

12. Method according to embodiment 10, wherein the automated system is characterised by being performed in a commercially available automated system, preferably in the Architect Immunoassay Analyzer (Abbott); Vidas Immunoanalyzer (Biomerieux); Cobas and Elecsys automated Immunoassay-Analyzers (Roche Diagnostics); Liaision Analyzer (Diasorin); or Euroimmun Analyzers (Euroimmun).

13. Kit for performing the method according to any one of embodiments 1 to 12, comprising:
   a solid support comprising immobilised IgM-binding molecules and
   a complex comprising
      (i) an antiparallel dimer of soluble flavivirus Protein E (sE) and
      (ii) a marker.

14. Kit according to embodiment 13, further comprising means to detect the marker, preferably means for detecting an affinity marker, a fluorescence marker, a radioactive marker, a chromogenic marker, a luminescence marker, or a magnetic marker.

15. Kit according to embodiment 13 or 14, further comprising a sample or a container containing a sample.

16. Kit according to any one of embodiments 13 to 15, further comprising a standard comprising IgM antibodies specific for a flavivirus.

17. Kit according to any one of embodiments 13 to 16, wherein the kit further comprises sE of a flavivirus distantly related to the important human pathogenic flaviviruses, preferably sE of Rio Bravo, Modoc, Yokose, Entebbe bat, Barkedji, or Lammi viruses, especially sE of Rio Bravo.

18. Kit according to any one of embodiments 13 to 17, wherein the kit further comprises an automated detection system, preferably comprising a sample conveying device, a detection device, a computer processing unit and/or a display for displaying the signal from the detection unit processed by computer software programs executed with the computer processing unit.

19. Kit according to any one of embodiments 13 to 18, wherein the kit is combined with a commercially available automated system, preferably with the Architect Immunoassay Analyzer (Abbott); Vidas Immunoanalyzer (Biomerieux); Cobas and Elecsys automated Immunoassay-Analyzers (Roche Diagnostics); Liaision Analyzer (Diasorin); or Euroimmun Analyzers (Euroimmun).

20. Kit according to any one of embodiments 13 to 19 wherein at least the solid support and/or the complex and/or the sE and the marker are packed in a sterile wrap, preferably in a sterile transparent plastic wrap.

REFERENCES

1. Allison, S. L., J. Schalich, K. Stiasny, C. W. Mandl, C. Kunz, and F. X. Heinz. 1995. Oligomeric rearrangement of tick-borne encephalitis virus envelope proteins induced by an acidic pH. J Virol 69:695-700.
2. Elshuber, S., S. L. Allison, F. X. Heinz, and C. W. Mandl. 2003. Cleavage of protein prM is necessary for infection of BHK-21 cells by tick-borne encephalitis virus. J Gen Virol 84:183-91.
3. Heinz, F. X., and C. Kunz. 1981. Homogeneity of the structural glycoprotein from European isolates of tick-borne encephalitis virus: comparison with other flaviviruses. J Gen Virol 57:263-74.
4. Heinz, F. X., M. Roggendorf, H. Hofmann, C. Kunz, and F. Deinhardt. 1981. Comparison of two different enzyme immunoassays for detection of immunoglobulin M antibodies against tick-borne encephalitis virus in serum and cerebrospinal fluid. J Clin Microbiol 14:141-6.
5. Jarmer, J., J. Zlatkovic, G. Tsouchnikas, O. Vratskikh, J. Strauss, J. H. Aberle, V. Chmelik, M. Kundi, K. Stiasny, and F. X. Heinz. 2014. Variation of the specificity of the human antibody responses after tick-borne encephalitis virus infection and vaccination. J Virol 88:13845-57. doi: 10.1128/JVI.02086-14
6. Kanai, R., K. Kar, K. Anthony, L. H. Gould, M. Ledizet, E. Fikrig, W. A. Marasco, R. A. Koski, and Y. Modis. 2006. Crystal Structure of West Nile Virus Envelope Glycoprotein Reveals Viral Surface Epitopes. J. Virol. 80:11000-11008.
7. Li, L., S. M. Lok, I. M. Yu, Y. Zhang, R. J. Kuhn, J. Chen, and M. G. Rossmann. 2008. The flavivirus precursor membrane-envelope protein complex: structure and maturation. Science 319:1830-4.
8. Luca, V. C., J. AbiMansour, C. A. Nelson, and D. H. Fremont. 2012. Crystal structure of the Japanese encephalitis virus envelope protein. J Virol 86:2337-46. doi: JVI.06072-11 [pii] 10.1128/JVI.06072-11
9. Maizel, J. V., Jr. 1971. Polyacrylamide gel elctrophoresis of viral proteins. Methdos Virol 5:179-246.
10. Modis, Y., S. Ogata, D. Clements, and S. C. Harrison. 2003. A ligand-binding pocket in the dengue virus envelope glycoprotein. Proc Natl Acad Sci USA 100:6986-91.
11. Modis, Y., S. Ogata, D. Clements, and S. C. Harrison. 2005. Variable surface epitopes in the crystal structure of dengue virus type 3 envelope glycoprotein. J Virol 79:1223-31. doi: 10.1128/JVI.79.2.1223-1231.2005
12. Musso, D., and D. J. Gubler. 2016. Zika Virus. Clinical Microbiology Reviews 29:487-524. doi: 10.1128/cmr.00072-15
13. Nybakken, G. E., C. A. Nelson, B. R. Chen, M. S. Diamond, and D. H. Fremont. 2006. Crystal Structure of the West Nile Virus Envelope Glycoprotein. J. Virol. 80:11467-11474.
14. Peeling, R. W., H. Artsob, J. L. Pelegrino, P. Buchy, M. J. Cardosa, S. Devi, D. A. Enria, J. Farrar, D. J. Gubler, M. G. Guzman, S. B. Halstead, E. Hunsperger, S. Kliks, H. S. Margolis, C. M. Nathanson, V. C. Nguyen, N. Rizzo, S. Vazquez, and S. Yoksan. 2010. Evaluation of diagnostic tests: dengue. Nat Rev Micro.
15. Rey, F. A., F. X. Heinz, C. Mandl, C. Kunz, and S. C. Harrison. 1995. The envelope glycoprotein from tick-borne encephalitis virus at 2 A resolution. Nature 375:291-8.
16. Simmonds, P., P. Becher, M. S. Collett, E. A. Gould, F. X. Heinz, G. Meyers, T. Monath, A. Pletnev, C. M. Rice, K. Stiasny, H. J. Thiel, A. Weiner, and J. Bukh. 2011. Family Flaviviridae, p. 1003-1020. In A. M. Q. King, E. Lefkowitz, M. J. Adams, and E. B. Carstens (ed.), Virus Taxonomy. IXth Report of the International Committee on Taxonomy of Viruses. Elsevier Academic Press, San Diego.
17. Stiasny, K., J. H. Aberle, V. Chmelik, U. Karrer, H. Holzmann, and F. X. Heinz. 2012. Quantitative determination of IgM antibodies reduces the pitfalls in the serodiagnosis of tick-borne encephalitis. J Clin Virol 54:115-20. doi: S1386-6532(12)00065-0 [pii] 10.1016/j.jcv.2012.02.016
18. Tsouchnikas, G., J. Zlatkovic, J. Jarmer, J. Strauss, O. Vratskikh, M. Kundi, K. Stiasny, and F. X. Heinz. 2015. Immunization with Immune Complexes Modulates the Fine-Specificity of Antibody Responses to a Flavivirus Antigen. J Virol. doi: 10.1128/JVI.00938-15
19. Zlatkovic, J., K. Stiasny, and F. X. Heinz. 2011. Immunodominance and functional activities of antibody responses to inactivated West Nile virus and recombinant subunit vaccines in mice. J Virol 85:1994-2003. doi: JVI.01886-10 [pii] 10.1128/JVI.01886-10

20. Zlatkovic, J., G. Tsouchnikas, J. Jarmer, C. Koessl, K. Stiasny, and F. X. Heinz. 2013. Aluminum hydroxide influences not only the extent but also the fine specificity and functional activity of antibody responses to tick-borne encephalitis virus in mice. J Virol 87:12187-95. doi: JVI.01690-13 [pii] 10.1128/JVI.01690-13
21. Mandl et al. 1989, J. Virol. 63:564-571
22. Zhang et al. 2004, Structure 12:1607-1618
23. Dai et al. 2016, Cell Host % Microbe 19:696-704
24. Kimple et al. 2015, Curr. Protoc. Protein Sci. 73: Unit-9.9. doi:10.1002/0471140864.ps0909s73
25. Wood 2014, Curr. Opin. Struc. Biol. 26:54-61
26. Koppel et al. 2001, J. Biochem. Biophys. Methods 49:641-647

The invention claimed is:

1. A method for the detection of an IgM antibody specific for a flavivirus in a sample, comprising:
- (a) contacting the sample with a solid support comprising immobilised IgM-binding molecules,
- (b) allowing binding of IgM antibodies in the sample to the IgM binding molecules on the solid support so that the IgM antibodies are also immobilised on the solid support, and
- (c) premixing an antiparallel dimer of soluble flavivirus Protein E (sE) with a marker for formation of a complex comprising the sE dimer and the marker, wherein the antiparallel dimer of sE comprises a tag and wherein the tag links the marker to the antiparallel dimer of sE, and
- (d) detecting IgM antibodies specific for a flavivirus by allowing binding of the preformed complex and identifying the binding of the complex to the specific flavivirus IgM antibody by detecting the marker.

2. The method according to claim 1, wherein the IgM-binding molecules are anti-IgM antibodies or IgM-binding fragments thereof.

3. The method according to claim 1, wherein the flavivirus is selected from group tick-borne encephalitis virus (TBEV) or dengue virus (DENV).

4. The method according to claim 1, wherein the sample is a serum or plasma sample, or a cerebrospinal fluid (CSF) sample.

5. The method according to claim 1, wherein the tag is selected from Strep-tag or His-tag.

6. The method according to claim 1, wherein the marker is selected from an affinity marker, a fluorescence marker, a radioactive marker, a nucleic acid marker, a chromogenic marker, a luminescence marker, a magnetic marker, or combinations thereof.

7. The method according to claim 1, wherein the complex comprises a labelled antibody and/or a Strep-tag binding protein.

8. The method according to claim 1, wherein the solid support is a microtiter plate or other plastic containers or surfaces, a biological microchip, a bead, a disc, a magnetic particle, a fiber optic sensor, a glass slide, or a membrane, preferably a nitrocellulose membrane, a polytetrafluorethylene membrane, a cellulose acetate membrane or a cellulose nitrate membrane.

9. The method according to claim 1, wherein detecting the marker comprises the addition of further substances thereby generating a signal or activating the marker to elicit a signal and measuring the signal.

10. The method according to claim 1, wherein sE of a flavivirus distantly related to the important human pathogenic flaviviruses is applied as a control.

11. The method according to claim 1, wherein the method is performed in an automated system.

12. A kit comprising:
- a solid support comprising immobilised IgM-binding molecules; and
- a complex comprising:
  - (i) an antiparallel dimer of soluble flavivirus Protein E (sE); and
  - (ii) a marker, for performing the method according to claim 1.

13. The kit of claim 12, further defined as comprising means to detect the marker.

14. The kit of claim 12, further defined as comprising an automated detection system.

15. The kit of claim 12, wherein at least the solid support and/or the complex and/or the sE and the marker are packed in a sterile wrap.

16. The method of claim 3, wherein the flavivirus is selected from DENV serotype 1 (DEN1), DENV serotype 2 (DEN2), DENV serotype 3 (DEN3), and DENV serotype 4 (DEN4), and Zika virus (ZV).

17. The method of claim 7, wherein the complex comprises a labelled antibody specific for a tag of the antiparallel dimer of sE and/or a Strep-tag binding protein comprising a marker further defined as an affinity marker, a fluorescence marker, a radioactive marker, a nucleic acid marker, a chromogenic marker, a luminescence marker, a magnetic marker, or combination thereof.

18. The method of claim 10, wherein the control is sE of Rio Bravo, Modoc, Yokose, Entebbe bat, Barkedji, or Lammi viruses.

19. The kit of claim 13, further defined as comprising means for detecting an affinity marker, a fluorescence marker, a radioactive marker, a chromogenic marker, a luminescence marker, or a magnetic marker.

20. The kit of claim 14, wherein the automated detection system is further defined as comprising a sample conveying device, a detection device, a computer processing unit and/or a display for displaying the signal from the detection unit processed by computer software programs executed with the computer processing unit.

* * * * *